(12) United States Patent
Brandt et al.

(10) Patent No.: US 10,370,493 B2
(45) Date of Patent: Aug. 6, 2019

(54) POLYGLYCEROL ALKOXYLATE ESTERS AND PREPARATION AND USE THEREOF

(71) Applicant: Evonik Degussa GmbH, Essen (DE)

(72) Inventors: Kathrin Daniela Brandt, Düsseldorf (DE); Matthias Lobert, Essen (DE); Dominik Schuch, Düsseldorf (DE); Joachim Venzmer, Essen (DE); Peter Schwab, Essen (DE); Beata Bednorz, Essen (DE); Anja Brösgen, Essen (DE); Svenja Blaschek, Gelsenkirchen (DE)

(73) Assignee: Evonik Degussa GmbH, Essen (GB)

( * ) Notice: Subject to any disclaimer, the term of this patent is extended or adjusted under 35 U.S.C. 154(b) by 111 days.

(21) Appl. No.: 15/380,001

(22) Filed: Dec. 15, 2016

(65) Prior Publication Data
US 2017/0218120 A1    Aug. 3, 2017

(30) Foreign Application Priority Data

Jan. 29, 2016   (EP) .................... 16153288

(51) Int. Cl.
| C08G 65/34 | (2006.01) |
| A61K 8/39 | (2006.01) |
| A61K 8/86 | (2006.01) |
| A61Q 19/10 | (2006.01) |
| A61Q 90/00 | (2009.01) |

(52) U.S. Cl.
CPC ............. *C08G 65/34* (2013.01); *A61K 8/39* (2013.01); *A61K 8/86* (2013.01); *A61Q 19/10* (2013.01); *A61Q 90/00* (2013.01); *A61K 2800/10* (2013.01); *A61K 2800/48* (2013.01); *C08G 2650/32* (2013.01); *C08G 2650/54* (2013.01)

(58) Field of Classification Search
CPC ............ C08G 2650/32; C08G 2650/54; C08G 65/34; A61K 2800/48; A61K 8/86
See application file for complete search history.

(56) References Cited

U.S. PATENT DOCUMENTS

| 4,614,622 | A | 9/1986 | Huettinger et al. |
| 4,895,681 | A | 1/1990 | Herrmann et al. |
| 6,156,298 | A | 12/2000 | Karlen et al. |
| 6,368,581 | B1 | 4/2002 | Karlen et al. |
| 7,553,495 | B2 | 6/2009 | Loeffler et al. |
| 7,709,011 | B2 | 5/2010 | Klug et al. |
| 8,993,792 | B2 | 3/2015 | Hartung et al. |
| 9,409,853 | B2 | 8/2016 | Schuch et al. |
| 2004/0143057 | A1 | 7/2004 | Ahrens et al. |
| 2008/0004357 | A1 | 1/2008 | Meyer et al. |
| 2014/0312273 | A1 | 10/2014 | Wattebled et al. |
| 2016/0311961 | A1 | 10/2016 | Klostermann et al. |

FOREIGN PATENT DOCUMENTS

| DE | 2024051 A1 | 12/1971 |
| DE | 3239564 C | 5/1984 |
| DE | 19753108 A1 | 8/1999 |
| DE | 10124547 A1 | 11/2002 |
| EP | 0264826 A2 | 4/1988 |
| EP | 0809527 A1 | 12/1997 |
| EP | 0919219 A2 | 6/1999 |
| EP | 1055407 A2 | 11/2000 |
| EP | 1344518 A2 | 9/2003 |
| EP | 1518900 A2 | 3/2005 |
| GB | 1333475 | 10/1973 |
| WO | 9625215 A1 | 8/1996 |
| WO | 0108481 A1 | 2/2001 |

OTHER PUBLICATIONS

German language Search Report dated May 19, 2016 in EP 16 15 3288 (7 pages).
Schuch et al., U.S. Appl. No. 15/346,855, filed Nov. 9, 2016.

*Primary Examiner* — Kortney L. Klinkel
(74) *Attorney, Agent, or Firm* — Philip P. McCann; Nexsen Pruet PLLC

(57) ABSTRACT

The invention provides polyglycerol alkoxylate esters and for the preparation and use thereof.

20 Claims, No Drawings

POLYGLYCEROL ALKOXYLATE ESTERS AND PREPARATION AND USE THEREOF

This application claims the benefit of European Application No. 16153288.2 filed on Jan. 29, 2016, the disclosure of which is expressly incorporated herein by reference.

FIELD OF THE INVENTION

The invention provides polyglycerol alkoxylate esters and for the preparation and use thereof.

BACKGROUND

The substance class of glycerol alkoxylate esters and polyglycerol alkoxylate esters is known, and various applications for this substance class have been described. These include use as antifoams as disclosed in EP0809527 and EP0264826, as emulsifiers in emulsion polymerization as disclosed in DE10124547, as an ingredient of pesticide preparations as disclosed in WO 0108481, and use in the cosmetics sector as thickener, solubilizers, conditioners and refatting agents, as disclosed, for example, in DE3239564, DE19753108 and DE2024051. The corresponding glycerol ester ethoxylates are used on the market as standard refatting agents (e.g. PEG-7 Glyceryl Cocoate=TEGOSOFT GC) and thickeners (e.g. PEG-200 Hydrogenated Glyceryl Palmate=REWODERM LI S 80) in aqueous surfactant formulations.

The prior art also describes polyglycerol alkoxylate esters as thickeners of cosmetic rinse-off formulations: For instance, EP1344518 discloses cosmetic and pharmaceutical formulations comprising an alkoxylated polyglycerol ester having a polymerization level of the polyglycerol of 1 to 30, with 50 to 250 alkoxy units per molecule, and EP1518900 discloses compositions comprising a) one or more alkoxylated polyglycerol esters having a polymerization level of the polyglycerol of 1.5 to 10, with 50 to 250 alkoxy units per molecule, b) an organic solvent or organic solvent mixture, and c) water.

In spite of a broad available range of thickeners for aqueous surfactant systems, there continues to be great interest on the market side in novel thickeners that are even more efficient. Specifically the provision of easily dosable and highly efficient thickeners offers considerable advantages to the user. Specifically the latter point makes it possible for the user to produce the same thickening effect with smaller amounts of active ingredient and hence conserve resources. The problem addressed by the present patent specification was thus that of providing novel, highly efficient and easily dosable thickeners.

SUMMARY

It has been found that, surprisingly, polyglycerol alkoxylate esters having more than 250 alkoxy units and having three or more acyl radicals per molecule function as significantly more effective thickeners of aqueous surfactant systems than the structures described in the prior art.

The present invention therefore provides polyglycerol alkoxylate esters having more than 250 alkoxy units and having three or more acyl radicals per molecule, and for the preparation and use thereof.

One advantage of the present invention is the improved thickening performance of the polyglycerol alkoxylate esters according to the invention compared to ethoxylate esters that are already known and customary on the market in aqueous surfactant formulations. Accordingly, higher viscosities in aqueous surfactant formulations with analogous composition can be achieved in the presence of the polyglycerol alkoxylate esters according to the invention than with non-inventive thickeners. On exchange of a thickener customary on the market for a polyglycerol alkoxylate ester according to the invention, therefore, with equal surfactant concentration, a smaller amount of the polyglycerol alkoxylate ester according to the invention is required to obtain an unchanged viscosity. Alternatively, on exchange of the same amount of non-inventive ethoxylate esters for the polyglycerol alkoxylate esters according to the invention, the amount of the surfactants used or the amount of sodium chloride in the formulation can also be reduced without loss of viscosity. Accordingly, the polyglycerol alkoxylate esters according to the invention thus generally enable a reduction in the total concentration of an aqueous surfactant formulation, resulting in enhanced efficiency. Furthermore, reduced primary surfactant and salt contents have an advantageous effect on the mildness, skinfeel and corrosivity of the respective surfactant formulations.

A further advantage of the polyglycerol alkoxylate esters described here is that they can produce a pleasant skinfeel in cosmetic formulations.

A further advantage is that the polyglycerol alkoxylate esters described here can alleviate irritation by surfactant formulations.

A further advantage of the polyglycerol alkoxylate esters described here is that they can be incorporated into aqueous surfactant formulations at 20 to 25° C. without supply of thermal energy.

A further advantage is that the polyglycerol alkoxylate esters described here have high water solubility and hence enable the production of glass-clear surfactant formulations.

A further advantage of the products according to the invention is that they exhibit very low foam formation while stirring in water.

Another advantage is that the polyglycerol alkoxylate esters described here do not affect the foamability and amount of foam formed by surfactant formulations, but can improve the creaminess of the foam.

A further advantage of the products according to the invention is that they have good stability to oxidation and hence are stable in terms of colour, odour and appearance.

DETAILED DESCRIPTION

The present invention therefore provides polyglycerol alkoxylate esters of the general formula (I)

general formula (I)

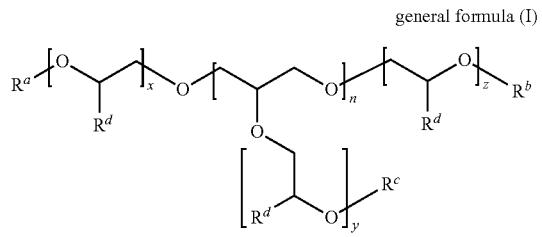

with $R^a$, $R^b$, $R^c$=identical or different and independently selected from H and acyl radical of an organic acid, preferably H and acyl radical of a fatty acid, more preferably H and acyl radical of a fatty acid having 16 to 22 carbon atoms, with the proviso that an average of 3 to 6, more preferably 3.5 to 5.5 and especially preferably 4 to 5 of the $R^a$, $R^b$, $R^c$ radicals per molecule are not H, $R^d$=identical or different and independently selected from H, alkyl- and aryl-, preferably H, methyl-, ethyl-, more preferably H and methyl, especially H, n=1 to 16, preferably 2 to 14, more preferably 3 to 11, most preferably 4 to 9, x, y, z=identical or different and independently 0 to 200, preferably 30 to 100, more preferably 40 to 80, with the proviso that the sum total of x+n y+z for each molecule averages 251 to 750, preferably 300 to 600, more preferably 350 to 550.

The polyglycerol alkoxylate esters according to the invention are mixtures of different substances; it will therefore be clear to the person skilled in the art that the numeric values specified may be average values over the mixture.

In the context of the present invention and as represented in the general formula (I), the term "polyglycerol" should be understood to mean a polyglycerol which may also contain glycerol. Consequently, for the purposes of calculating amounts, masses and the like, any glycerol fraction should also be taken into consideration. Owing to its polymeric property, the polyglycerol is a statistical mixture of various compounds. Polyglycerol may have ether bonds formed between two primary, one primary and one secondary or else two secondary positions of the glycerol monomers. For this reason, the polyglycerol base skeleton does not usually consist exclusively of linearly linked glycerol units, but may also comprise branches and rings. For details see, for example, "*Original synthesis of linear, branched and cyclic oligoglycerol standards*", Cassel et al., *J. Org. Chem.* 2001, 875-896. Structures of this kind are covered by the general formula (I) which has been simplified in this respect.

It is apparent that the $R^c$ radicals present n times may be the same or different from one another. The index y present n times in the n units may likewise be the same or different.

Parameters or measurements are preferably determined using the methods described hereinbelow. In particular, these methods are used in the examples of the present intellectual property right.

In the context of this invention, weight-average and number-average molecular weights are determined for the polyglycerol alkoxylates and polyglycerol alkoxylate esters prepared by gel permeation chromatography (GPC) calibrated against a polypropylene glycol standard. GPC was performed using an Agilent 1100 instrument fitted with an RI detector and an SDV 1000/10000 Å column combination consisting of an 0.8 cm×5 cm pre-column and two 0.8 cm×30 cm main columns at a temperature of 30° C. and a flow rate of 1 ml/min (mobile phase: THF). The sample concentration was 10 g/l and the injection volume was 20 µl. The polydispersity corresponds to the quotient $M_w$ divided by $M_n$ (PDI=$M_w/M_n$).

The alkoxylation level is determined by utilizing $^1$H NMR spectroscopy. The NMR spectra are measured with a Bruker 400 MHz spectrometer using a QMP head. The sample to be analysed is dissolved in a suitable deuterated solvent (e.g. methanol) and transferred into 5 mm or, if appropriate, 10 mm NMR tubes.

The characteristic proton signals of an illustrative polyglycerol alkoxylate ester according to the invention are shown in the schematic diagram which follows, which corresponds to a simplified representation of formula (I) that shows, for reasons of clarity, exclusively stearic acid as fatty acid fragment and ethylene oxide, also abbreviated hereinafter as EO, as alkylene oxide monomer. The elucidations which follow can also be applied mutatis mutandis to structures containing other fatty acids or alkylene oxides as monomer units.

As well as the individual characteristic fragments (shown from left to right) of fatty acid (stearic acid), ethylene oxide and (poly)glycerol fragment, the characteristic protons with the indices $H^a$ to $H^j$ are also mentioned, as are the shifts thereof in the $^1$H NMR spectrum. The NMR was calibrated to the solvent signal, in the specific case to the methanol signal at 3.3 ppm.

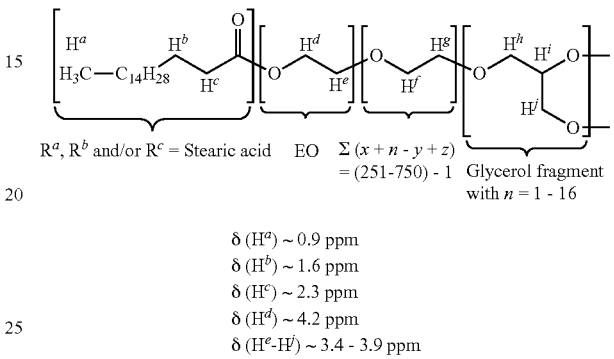

$R^a$, $R^b$ and/or $R^c$ = Stearic acid   EO   $\Sigma (x + n \cdot y + z)$
$\phantom{xxxxxxxxxxxxxxxxxxxxxxxxxxxxxxx}$ = (251-750) - 1   Glycerol fragment
$\phantom{xxxxxxxxxxxxxxxxxxxxxxxxxxxxxxxxxxxxxxxxxxxxxxx}$ with $n = 1$ - 16

$\delta (H^a) \sim 0.9$ ppm
$\delta (H^b) \sim 1.6$ ppm
$\delta (H^c) \sim 2.3$ ppm
$\delta (H^d) \sim 4.2$ ppm
$\delta (H^e\text{-}H^j) \sim 3.4$ - 3.9 ppm Quantitative esterification of the fatty acids can be inferred from the integral ratios of the signals of the $H^a$, $H^b$ and/or $H^c$ groups of the acyl radicals to the signal of the $H^d$ group of the acylated ethylene oxide units of the polyalkylene oxide chains. All signals have the same integral values per hydrogen atom of the respective group within the scope of measurement accuracy of the method (integration error about 5%).

The alkoxylation level can be calculated from the integral ratios of the $H^e$ to $H^j$ signal group, for example, to the signals of the $H^a$ or $H^c$ group. Preferably, the $H^a$ signal is used as a representative signal for the fatty acid residue for the calculation of the alkoxylation level.

However, the mathematical calculation of the number of protons of the alkylene oxide units of the $H^e$ to $H^j$ signal group should take account of the (poly)glycerol protons in the assessment, and likewise that the $H^d$ protons, which of course also come from the alkylene oxide, give rise to a separate signal.

If, for example, a tetrastearate of polyglycerol-5 with 400 mol of EO is present, the assessment can be made as follows: The integral of the $H^a$ signal has to be divided by 12 (4 molar equivalents of fatty acid each having one $CH_3$ group) in order to ascertain the proportion corresponding to one proton. If the integral of the $H^e$ to $H^j$ signal group is then divided by the integral proportion ascertained above that corresponds to one proton, the number of protons of this signal group is found. It is then necessary to subtract the number of protons of the (poly)glycerol from this value (i.e. minus 25, since 5 mol of glycerol each having 5 hydrogens are present), and the remaining protons, taking account of the integral of the $H^d$ signal, give the totality of all ethylene oxide signals. If this number is divided by four (1 mol of EO contains 4 protons), the ethoxylation level is finally obtained in the specific case.

Wet-chemical analyses are conducted by international standard methods (acid number: DGF C-V 2, Ph. Eur. 2.5.1; hydroxyl number: DGF C-V 17 a (53), Ph. Eur. 2.5.3 method A; hydrolysis number: DGF C-V 3, Ph. Eur. 2.5.6).

The polymerization level n can be ascertained by the hydroxyl number of the polyglycerol, where the mean polymerization level n is linked to the hydroxyl number of the underlying polyglycerol via the following equation:

$$n = \frac{\frac{2000 \cdot M(\text{KOH})}{\text{OHN}} - M(\text{Water})}{\left[ [M(\text{Glycerol}) - M(\text{Water})] - \frac{1000 \cdot M(\text{KOH})}{\text{OHN}} \right]} \quad \text{formula (II)}$$

where M=molar mass; OHN=hydroxyl number of the free polyglycerol.

Unless otherwise stated, all percentages (%) given are percentages by weight.

Preferred polyglycerol alkoxylate esters of the present invention have $R^a$, $R^b$, $R^c$ radicals in which at least 40% of the acyl radicals contain 18 carbon atoms, very particular preference being given to stearic acid residues, where the percentages are based on the numerical number of all $R^a$, $R^b$, $R^c$ radicals present in the polyglycerol alkoxylate ester.

Preferred polyglycerol alkoxylate esters of the present invention are characterized in that
$R^a$, $R^b$, $R^c$=H or acyl radical of a fatty acid having 16 to 22 carbon atoms,
with the proviso that an average of 3.5 to 6 of the $R^a$, $R^b$, $R^c$ radicals per molecule are not H,
$R^d$=H,
n=3 to 11,
x, y, z=identical or different and independently 30 to 200,
with the proviso that the sum total of x+n·y+z for each molecule averages 300 to 750.

Preferred polyglycerol alkoxylate esters of the present invention are characterized in that
$R^a$, $R^b$, $R^c$=H or acyl radical of a fatty acid having 16 to 22 carbon atoms,
with the proviso that an average of 4 to 5 of the $R^a$, $R^b$, $R^c$ radicals per molecule are not H,
$R^d$=H,
n=4 to 9,
x, y, z=40 to 80,
with the proviso that the sum total of x+n y+z for each molecule averages 350 to 550.

In this connection, it is especially preferable that the polyglycerol alkoxylate esters of the present invention have $R^a$, $R^b$, $R^c$ radicals where at least 40% of the acyl radicals in the fatty acid are stearic acid residues, where the percentages are based on the numerical number of all $R^a$, $R^b$, $R^c$ radicals present in the polyglycerol alkoxylate ester.

In principle, the polyglycerol alkoxylate esters according to the invention can be prepared by any desired methods which can be found in the prior art, for example EP1344518 and EP1518900.

Preferably, the polyglycerol alkoxylate esters of the invention are prepared by the process described hereinafter for preparing polyglycerol alkoxylate esters, which likewise forms part of the subject-matter of the present invention.

The process according to the invention for preparing polyglycerol alkoxylate esters comprises the process steps of
A) providing a polyglycerol having a polymerization level of 1.5 to 16, preferably 2 to 14, more preferably 3 to 11, most preferably 4 to 9,
B) alkoxylating with 251 to 750, preferably 300 to 600 and more preferably 350 to 550 mol of alkylene oxide selected from the group of ethylene oxide, propylene oxide, butylene oxide and dodecene oxide, especially ethylene oxide, per mole of polyglycerol used in the overall process, and
C) esterifying with 3 to 6, more preferably 3.5 to 5.5 and especially preferably 4 to 5 mol of at least one selected from organic acids, preferably fatty acids, especially fatty acids having 16 to 22 carbon atoms, per mole of polyglycerol used in the overall process.

The process according to the invention for preparing polyglycerol alkoxylate esters may comprise at least one further process step, for example
D) purifying the polyglycerol alkoxylate ester.

The polyglycerol for process step A) can be provided by various conventional methods, for example polymerization of glycidol (for example with base catalysis), polymerization of epichlorohydrin (for example in the presence of equimolar amounts of a base such as NaOH) or polycondensation of glycerol. The letter is effected, for example, in the presence of catalytic amounts of a base, for example NaOH or KOH. Suitable reaction conditions are temperatures between 220 and 260° C. and a reduced pressure within a range between 20 and 800 mbar, especially between 50 and 500 mbar, which enables easier removal of water. Corresponding methods can be found in standard chemistry textbooks, for example Römpp online, Thieme Verlag, updated 31 Dec. 2015.

Process step b), an alkoxylation, is a known synthesis in organic chemistry with adequately known process parameters and is described, for example, in the "Surfactants" and/or "Polyoxyalkylenes" chapters in Ullmann's Encyclopedia of Industrial Chemistry, and in "Alkylene_Oxides_and_Their_Polymers" by F. E. Bailey and J. V. Koleske, Marcel Dekker Inc. 1991.

Process step C), an esterification, is a known synthesis in organic chemistry with adequately known process parameters and is described in standard textbooks, for example the Organikum, Wiley-VCH publishers. Polyglycerol ester syntheses specifically are described in, for example, Fette, Seifen, Anstrichm. 82, 93 (1980) or Tenside, Deterg. 23, 320 (1986).

The process steps can be conducted in the process according to the invention in the "A), B), C)" or "A), C), B)" sequence, preference being given in accordance with the invention to "A), C), B)", since the polyglycerol alkoxylate esters obtainable in this way have elevated storage stability and less concentration-dependent thickening performance in aqueous surfactant formulations.

Preferred processes according to the invention are characterized in that
a polyglycerol having a polymerization level of 3 to 11 is used in process step A),
300 to 750 mol of ethylene oxide per mole of polyglycerol used in the overall process is used in process step B) and
3.5 to 6 mol of at least one selected from fatty acids having 16 to 22 carbon atoms per mole of polyglycerol used in the overall process is used in process step C).

Particularly preferred processes according to the invention are characterized in that
a polyglycerol having a polymerization level of 4 to 9 is used in process step A),
350 to 550 mol of ethylene oxide per mole of polyglycerol used in the overall process is used in process step B) and
4 to 5 mol of at least one selected from fatty acids having 16 to 22 carbon atoms per mole of polyglycerol used in the overall process is used in process step C).

In this connection, it is especially preferable that fatty acids having 16 to 22 carbon atoms are used, in which at least 40 mol %, based on all fatty acids having 16 to 22 carbon atoms, is stearic acid.

The polyglycerol alkoxylate esters obtainable by the process according to the invention have surprising performance properties and hence likewise form part of the subject-matter of the present invention, naturally with corresponding preference in accordance with the invention for polyglycerol alkoxylate esters obtainable by processes according to the invention identified as preferred above.

The polyglycerol alkoxylate esters according to the invention and the polyglycerol alkoxylate esters obtainable by the process according to the invention can advantageously be used in formulations, especially in the formulations according to the invention detailed hereinafter, for example as thickeners.

The invention thus further provides formulations comprising the polyglycerol alkoxylate esters according to the invention and/or the polyglycerol alkoxylate esters obtainable by the process according to the invention, where the formulations according to the invention are preferably aqueous formulations, especially aqueous surfactant formulations.

The expression "aqueous formulation" in connection with the present invention is understood to mean a formulation containing at least 5% by weight of water, based on the overall composition under consideration.

In the formulations according to the invention, preferably, no further polyglycerol alkoxylate esters are present apart from the polyglycerol alkoxylate esters according to the invention and/or the polyglycerol alkoxylate esters obtainable by the process according to the invention; if a preferred formulation according to the invention contains preferred polyglycerol alkoxylate esters and/or polyglycerol alkoxylate esters obtainable by a preferred process according to the invention, preferably only these polyglycerol alkoxylate esters are present in the formulation.

Preferred formulations according to the invention are characterized in that they contain the polyglycerol alkoxylate esters according to the invention and/or the polyglycerol alkoxylate esters obtainable by the process according to the invention in an amount of 0.01% by weight to 20% by weight, preferably 0.05% by weight to 10% by weight, especially 0.1% by weight to 5% by weight, where the percentages by weight are based on the overall composition.

An aqueous surfactant formulation according to the invention is characterized in that it additionally contains at least one surfactant, especially in a total amount of 0.1% by weight to 20% by weight, preferably 1.0% by weight to 15% by weight, especially 5.0% by weight to 10% by weight, where the percentages by weight relate to the overall composition.

In the context of the present invention, the term "surfactant" is understood to mean organic substances with interface-active properties which have the ability to reduce the surface tension of water at 20° C. and at a concentration of 0.5% by weight, based on the overall composition, to below 45 mN/m. The surface tension is determined here by the ring method in accordance with du Noüy at 25° C.

The surfactants are especially nonionic surfactants, anionic surfactants, cationic surfactants and amphoteric surfactants, the term "amphoteric surfactant" encompassing zwitterionic surfactants.

Preference is given to formulations according to the invention which are characterized in that the surfactant is selected from the group comprising, preferably consisting of:
anionic surfactants, nonionic surfactants and amphoteric surfactants, more preferably anionic surfactants and amphoteric surfactants.

If the formulation according to the invention comprises an anionic surfactant, preference is given in particular to formulations according to the invention which are characterized in that the anionic surfactant is selected from the group comprising, preferably consisting of:
alkyl sulphates and alkyl ether sulphates in the form of their alkali metal, alkaline earth metal, ammonium or alkanolammonium salts,
alkyl phosphates in the form of their alkali metal, ammonium or alkanolammonium salts,
alkyl ether carboxylates in the form of their alkali metal or ammonium salts,
acyl isethionates and acylalkyl isethionates in the form of their alkali metal or ammonium salts,
acyl sarcosinates in the form of their alkali metal or ammonium salts,
sulphosuccinates in the form of their alkali metal or ammonium salts and
acylglutamates in the form of their alkali metal or ammonium salts,
acylglycinates in the form of their alkali metal or ammonium salts,
acylalaninates in the form of their alkali metal or ammonium salts,
particular preference being given to alkyl sulphates and alkyl ether sulphates.

If the formulation according to the invention comprises an amphoteric surfactant, preference is given in particular to formulations according to the invention which are characterized in that the amphoteric surfactant is selected from the group comprising, preferably consisting of:
betaines, amphoacetates and amphopropionates, N-alkyl-N, N-dimethylammonium glycinates, for example an alkyldimethylammonium glycinate containing alkyl chains having 8 to 18 carbon atoms, preferably 12 to 16 carbon atoms, N-acylaminopropyl-N,N-dimethylammonium glycinates, for example an acylaminopropyldimethylammonium glycinate containing acyl radicals having 8 to 18 carbon atoms, 2-alkyl-3-carboxylmethyl-3-hydroxyethylimidazolines having 8 to 18 carbon atoms each in the alkyl or acyl group and an acylaminoethylhydroxyethylcarboxymethylglycinate having 8 to 18 carbon atoms in the acyl group,
compounds which, apart from a C8- to C18-alkyl or -acyl group in the molecule, contain at least one free amino group and at least one —COOH or —SO$_3$H group and are capable of forming internal salts, for example N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having 8 to 18 carbon atoms in the alkyl group, N-acylalkylaminopropionate, acylaminoethylaminopropionate, each containing acyl/alkyl radicals having 8 to 18 carbon atoms, and C12/18-acylsarcosine, particular preference being given to N-acylaminopropyl-N,N-dimethylammonium glycinates containing acyl radicals having 8 to 18 carbon atoms.

If the formulation according to the invention contains an anionic and/or amphoteric surfactant, preference is given especially to formulations according to the invention which are characterized in that they contain 0.1% to 5%, preferably 0.5% to 5%, salt, especially selected from alkali metal and alkaline earth metal halides, preference being given in accordance with the invention to sodium chloride.

In a further preferred embodiment of the formulations according to the invention, the formulation includes, as well as water and polyglycerol alkoxylate ester according to the invention, at least one optionally alkoxylated, especially ethoxylated, alcohol preferably having a boiling point of more than 150° C. at 1 bar. The latter is preferably selected from di- and polyhydric alcohols and fatty alcohol ethoxylates, more preferably selected from glycerol, propane-1,2- and -1,3-diol, dipropylene glycol and ethoxylated lauryl alcohol.

Instead of or in addition to the optionally alkoxylated alcohol, this further preferred formulation according to the invention may comprise at least one optionally alkoxylated, especially ethoxylated, carboxylic ester. These are preferably selected from fatty acid esters, especially polyol ethoxylate fatty acid esters, more preferably glycerol ethoxylate fatty acid esters, having an average of 5 to 10 ethylene glycol units.

In connection with this further preferred embodiment comprising at least one optionally alkoxylated alcohol and/or at least one optionally alkoxylated carboxylic ester, a preferred alternative formulation according to the invention is characterized in that it contains the polyglycerol alkoxylate esters according to the invention and/or the polyglycerol alkoxylate esters obtainable by the process according to the invention in an amount of 30% to 70% by weight, based on the overall formulation.

As already explained above, the present invention further provides for the use of the polyglycerol alkoxylate esters according to the invention and of the polyglycerol alkoxylate esters obtainable by the process according to the invention as thickeners for formulations, especially for the formulations according to the invention.

The present invention likewise provides for the use of the polyglycerol alkoxylate esters according to the invention and/or the polyglycerol alkoxylate esters obtainable by the process according to the invention and/or the formulations according to the invention for skincare.

The present invention likewise provides for the use of the polyglycerol alkoxylate esters according to the invention and/or the polyglycerol alkoxylate esters obtainable by the process according to the invention for foam stabilization of formulations, especially of the formulations according to the invention.

The present invention likewise provides for the use of the polyglycerol alkoxylate esters according to the invention and/or the polyglycerol alkoxylate esters obtainable by the process according to the invention for reducing irritation by cosmetic formulations, particularly on skin and/or eyes.

The examples presented below describe the present invention by way of example, without any intention of restricting the invention, the scope of application of which is apparent from the entirety of the description and the claims, to the embodiments specified in the examples.

EXAMPLES

Example 1: Preparation of Polyglycerol Esters 1.1 Preparation of polyglycerol-6 pentastearate Under a nitrogen atmosphere, 90.0 g of polyglycerol-6 from Spiga Nord (hydroxyl number=976 mg KOH/g) were stirred with 256 g of stearic acid (4.5 molar equiv.) at 240° C. until an acid number of <2 mg KOH/g was attained. The water formed over the course of the reaction was continuously distilled off. After cooling to room temperature, the reaction product was in the form of a yellowish solid.

1.2 Preparation of polyglycerol-6 penta(stearate/palmitate)

Under a nitrogen atmosphere, 216 g of polyglycerol-6 from Daicel (hydroxyl number=973 mg KOH/g) were stirred with a mixture of 300 g of stearic acid (2.2 molar equiv.) and 284 g of palmitic acid (2.3 molar equiv.) at 240° C. until an acid number of <2 mg KOH/g was attained. The water formed over the course of the reaction was continuously distilled off. After cooling to room temperature, the reaction product was in the form of a yellowish solid.

1.3 Preparation of polyglycerol-6 pentabehenate

Under a nitrogen atmosphere, 76.5 g of polyglycerol-6 from Spiga Nord (hydroxyl number=976 mg KOH/g) were stirred with 260 g of behenic acid (4.5 molar equiv.) at 240° C. until an acid number of <2 mg KOH/g was attained. The water formed over the course of the reaction was continuously distilled off. After cooling to room temperature, the reaction product was in the form of a yellowish solid.

1.4 Preparation of polyglycerol-3 tetra(stearate/palmitate)

Under a nitrogen atmosphere, 62 g of polyglycerol-3 from Solvay (hydroxyl number=1155 mg KOH/g) were stirred with a mixture of 139 g of stearic acid (2.0 molar equiv.) and 131 g of palmitic acid (2.0 molar equiv.) at 240° C. until an acid number of <2 mg KOH/g was attained. The water formed over the course of the reaction was continuously distilled off. After cooling to room temperature, the reaction product was in the form of a yellowish solid.

1.5 Preparation of polyglycerol-6 hexaoleate

Under a nitrogen atmosphere, 75 g of polyglycerol-6 from Daicel (hydroxyl number=973 mg KOH/g) were stirred with 280 g of oleic acid (6.0 molar equiv.) at 240° C. until an acid number of <2 mg KOH/g was attained. The water formed over the course of the reaction was continuously distilled off. After cooling to room temperature, the reaction product was in the form of a yellowish solid.

1.6 Preparation of polyglycerol-6 pentaoleate

Under a nitrogen atmosphere, 90 g of polyglycerol-6 from Daicel (hydroxyl number=973 mg KOH/g) were stirred with 280 g of oleic acid (5.0 molar equiv.) at 240° C. until an acid number of <2 mg KOH/g was attained. The water formed over the course of the reaction was continuously distilled off. After cooling to room temperature, the reaction product was in the form of a yellowish solid.

1.7 Preparation of polyglycerol-6 tetra(stearate/palmitate)

Under a nitrogen atmosphere, 90 g of polyglycerol-6 from Daicel (hydroxyl number=973 mg KOH/g) were stirred with a mixture of 108 g of stearic acid (1.9 molar equiv.) and 102 g of palmitic acid (2.0 molar equiv.) at 240° C. until an acid number of <2 mg KOH/g was attained. The water formed over the course of the reaction was continuously distilled off. After cooling to room temperature, the reaction product was in the form of a yellowish solid.

Example 2: Preparation of Polyglycerol Alkoxylate Esters

The polyglycerol alkoxylate esters A to H are inventive examples; the polyglycerol alkoxylate ester I is a non-inventive comparative example.
a.) By Means of Alkoxylation of Polyglycerol Esters 2.1 Preparation of polyglycerol-6-based Polyglycerol Alkoxylate Ester A with 450 Molar Equivalents of EO and 4.5 Molar Equivalents of Stearic Acid (Inventive)

A 5 liter autoclave was initially charged with 300 g of the polyglycerol ester from Example 1.1 together with 3 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 1638 g of ethylene oxide (EO) were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 959 g of EO were added at 150° C. onto the intermediate remaining in the reactor (908 g). On attainment of constant pressure and after final further reaction for 1 h, the product was deodorized at 95° C. as before.

A colourless to yellowish product which is solid at RT was obtained that had an OH number of 13.6 mg KOH/g and a hydrolysis number HN of 13 mg KOH/g and an AN of 0.1 mg KOH/g. By GPC, $M_w$=14522 g/mol, $M_n$=8225 g/mol, and the PDI was 1.77.

2.2 Preparation of polyglycerol-6-based Polyglycerol Alkoxylate Ester B with 450 Molar Equivalents of EO and 4.5 Molar Equivalents of C16/C18 Fatty Acid (Inventive)

A 5 liter autoclave was initially charged with 408 g of the polyglycerol ester from Example 1.2 together with 3 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 2125 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 692 g of EO were added at 130° C. onto the intermediate remaining in the reactor (661 g). On attainment of constant pressure and after final further reaction for 1 h, the product was deodorized at 95° C. as before.

A solid, colourless to yellowish product was obtained that had an OH number of 13.7 mg KOH/g and a hydrolysis number HN of 15 mg KOH/g and an AN of 0.1 mg KOH/g. By GPC, $M_w$=17059 g/mol, $M_n$=7085 g/mol, and the PDI was 2.11.

2.3 Preparation of polyglycerol-6-based Polyglycerol Alkoxylate Ester C with 450 Molar Equivalents of EO and 4.5 Molar Equivalents of Behenic Acid (Inventive)

A 5 liter autoclave was initially charged with 273 g of the polyglycerol ester from Example 1.3 together with 3 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 1294 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 591 g of EO were added at 170° C. onto the intermediate remaining in the reactor (573 g). On attainment of constant pressure and after final further reaction for 1 h, the product was deodorized at 95° C. as before.

A solid, colourless to yellowish product was obtained that had an OH number of 14.2 mg KOH/g and a hydrolysis number HN of 14 mg KOH/g and an AN of <0.1 mg KOH/g. By GPC, $M_w$=13594 g/mol, $M_n$=8350 g/mol, and the PDI was 1.63.

2.4 Preparation of polyglycerol-3-based Polyglycerol Alkoxylate Ester E with 300 Molar Equivalents of EO and 4.0 Molar Equivalents of C16/C18 Fatty Acid (Inventive)

A 5 liter autoclave was initially charged with 286.5 g of the polyglycerol ester from Example 1.4 together with 2 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 985 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 827 g of EO were added at 170° C. onto the intermediate remaining in the reactor (712 g). On attainment of constant pressure and after final further reaction for 1 h, the product was deodorized at 95° C. as before.

A solid, colourless to yellowish product was obtained that had an OH number of 10.4 mg KOH/g and a hydrolysis number HN of 11 mg KOH/g and an AN of 0.1 mg KOH/g. By GPC, $M_w$=11607 g/mol, $M_n$=7655 g/mol, and the PDI was 1.52.

2.5 Preparation of polyglycerol-6-based Polyglycerol Alkoxylate Ester F with 400 Molar Equivalents of EO and 6.0 Molar Equivalents of Oleic Acid (Inventive)

A 5 liter autoclave was initially charged with 328.6 g of the polyglycerol ester from Example 1.5 together with 3 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 1469 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 792 g of EO were added at 170° C. onto the intermediate remaining in the reactor (970 g). On attainment of constant pressure and after final further reaction for 1 h, the product was deodorized at 95° C. as before.

A solid, colourless to yellowish product was obtained that had an OH number of 12.0 mg KOH/g and a hydrolysis number HN of 14 mg KOH/g and an AN of 0.1 mg KOH/g. By GPC, $M_w$=14427 g/mol, $M_n$=8944 g/mol, and the PDI was 1.61.

2.6 Preparation of polyglycerol-6-based Polyglycerol Alkoxylate Ester G with 500 Molar Equivalents of EO and 5.0 Molar Equivalents of Oleic Acid (Inventive)

A 5 liter autoclave was initially charged with 309.1 g of the polyglycerol ester from Example 1.6 together with 3 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 1587 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 1011 g of EO were added at 170° C. onto the intermediate remaining in the reactor (805 g). On attainment of constant pressure and after final further reaction for 1 h, the product was deodorized at 95° C. as before.

A solid, colourless to yellowish product was obtained that had an OH number of 13.9 mg KOH/g and a hydrolysis number HN of 14 mg KOH/g and an AN of 0.1 mg KOH/g. By GPC, $M_w$=25490 g/mol, $M_n$=7040 g/mol, and the PDI was 3.62.

2.7 Preparation of polyglycerol-3-based Polyglycerol Alkoxylate Ester H with 400 Molar Equivalents of EO and 4.0 Molar Equivalents of C16/C18 Fatty Acid (Inventive)

A 5 liter autoclave was initially charged with 293.7 g of the polyglycerol ester from Example 1.7 together with 2 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 1744 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 967 g of EO were added at 170° C. onto the intermediate remaining in the reactor (1131 g). On attainment of constant pressure and after final further reaction for 1 h, the product was deodorized at 95° C. as before.

A solid, colourless to yellowish product was obtained that had an OH number of 13.2 mg KOH/g and a hydrolysis number HN of 14 mg KOH/g and an AN of 0.1 mg KOH/g. By GPC, $M_w$=20394 g/mol, $M_n$=6827 g/mol, and the PDI was 2.99.

b.) By Means of Esterification of Polyglycerol Ethoxylates

2.8 Preparation of polyglycerol-3-based Polyglycerol Alkoxylate Ester D with 300 Molar Equivalents of EO and 3.0 Molar Equivalents of Oleic Acid (Inventive)

2.8.1 Alkoxylation: A 5 liter autoclave was initially charged with 104.7 g of polyglycerol-3 (from Solvay) together with 2 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 3777 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 1148 g of EO were added at 170° C. onto the intermediate remaining in the reactor (2369 g). On attainment of constant pressure and after final further reaction for 1 h, the product was deodorized at 95° C. as before.

A solid, colourless to yellowish product was obtained that had an OH number of 22.0 mg KOH/g and an AN of 0.2 mg KOH/g. By GPC, $M_w$=11761 g/mol, $M_n$=10359 g/mol, and the PDI was 1.14.

2.8.2 Esterification: Under a nitrogen atmosphere and a reduced pressure of 50 mbar, 255 g of the ethoxylate from Example part 2.8.1 were stirred with 16.7 g of oleic acid (3.0 molar equiv.) at 140° C. until an acid number of <3 mg KOH/g had been attained. The water formed over the course of the reaction was continuously distilled off. After cooling down to room temperature, the reaction product was in the form of a colourless solid and had an acid number of 2.6 mg KOH/g, a hydroxyl number of 13 mg KOH/g and a hydrolysis number of 18 mg KOH/g.

2.9 Preparation of polyglycerol-3-based Polyglycerol Alkoxylate Ester I with 250 Molar Equivalents of EO and 2.0 Molar Equivalents of Oleic Acid (Non-Inventive)

2.9.1 Alkoxylation: A 5 liter autoclave was initially charged with 167.1 g of polyglycerol-3 (from Solvay) together with 2 mol % of aqueous KOH solution (45%). The reactor was inertized by injecting nitrogen to 3 bar and then decompressing to standard pressure. This operation was repeated twice more. While stirring, the contents of the reactor were heated to 150° C. and evacuated to about 20 mbar in order to remove the water from the catalysis step by distillation. Then 3012 g of EO were added on at a temperature of 170° C. in such a way that the pressure in the reactor did not rise above 4 bar gauge. The end of the metered addition was followed by a wait period until the pressure ceased to fall any further. On attainment of this constant pressure, further reaction was conducted at 170° C. for another one hour. Subsequently, the reaction mixture was cooled down to 95° C. and deodorized by application of a pressure (p<20 mbar) with stirring for about 15 minutes in order to remove traces of unconverted alkylene oxide. Then the product was partly discharged. Subsequently, a further 692 g of EO were added at 170° C. onto the intermediate remaining in the reactor (653 g). On attainment of constant pressure and after final further reaction for 1 h, the product was deodorized at 95° C. as before.

A solid, colourless to yellowish product was obtained that had an OH number of 15.3 mg KOH/g and an AN of –0.15 mg KOH/g. By GPC, $M_w$=15330 g/mol, $M_n$=12720 g/mol, and the PDI was 1.21.

2.9.2 Esterification: Under a nitrogen atmosphere, 217 g of the ethoxylate from Example part 2.9.1 were stirred with 7.30 g of oleic acid (2.0 molar equiv.) at 140° C. and 50 mbar until an acid number of <3 mg KOH/g had been attained. The water formed over the course of the reaction was continuously distilled off. After cooling down to room temperature, the reaction product was in the form of a colourless solid and had an acid number of 1.7 mg KOH/g, a hydroxyl number of 10 mg KOH/g and a hydrolysis number of 10 mg KOH/g.

Example 3: Application Examples

Example 3.1: Improved Thickening Performance of the Polyglycerol Alkoxylate Esters According to the Invention Compared to Non-Inventive Ethoxylate Esters in Aqueous Surfactant Solutions with Market Standard Surfactant Concentration The thickening action of the inventive polyglycerol alkoxylate ester prepared was evaluated in comparison with non-inventive polyglycerol alkoxylate esters prepared in-house and in comparison with commercially available thickeners in cosmetic formulations. The constituents of the formulations are named in the compositions in the form of the generally recognized INCI nomenclature using the English terms. The percentages are understood to mean percent by weight.

The commercially available thickeners used were the following:

1. REWODERM® LI S 80:

Standard thickener based on glycerol ethoxylate ester,

INCI: PEG-200 Hydrogenated Glyceryl Palmate (and) PEG-7 Glyceryl Cocoate

2. ANTIL® 200:

Standard thickener based on glycerol ethoxylate ester,

INCI: PEG-200 Hydrogenated Glyceryl Palmate (and) PEG-7 Glyceryl Cocoate

3. ANTIL® 120 Plus:

Standard thickener based on methylglucose ethoxylate ester,

INCI: PEG-120 Methyl Glucose Dioleate

4. Genapol® LT:

Standard thickener based on diglycerol ethoxylate ester,

INCI: PEG-150 Polyglyceryl-2 Tristearate (and) Laureth-3 (and) Dipropylene Glycol In order to examine the thickening performance of the polyglycerol alkoxylate ester according to the invention, defined amounts of these products were incorporated into surfactant systems by stirring at room temperature and then the viscosities were measured.

Table 1 compares the improved thickening performance of the polyglycerol alkoxylate esters according to the invention with the thickening performance of market standard ethoxylate esters:

TABLE 1

Measured viscosities in mPa s (Brookfield viscometer, 25° C.) of an aqueous surfactant solution containing 12% by weight of a mixture of Sodium Laureth Sulfate and Cocamidopropylbetaine (weight ratio 9:3) and 0.7% sodium chloride and thickener in the amount specified; adjusted to pH 5.5

| Thickener used | Thickener concentration | | | | | |
|---|---|---|---|---|---|---|
| | 0.3% by wt. | 0.4% by wt. | 0.5% by wt. | 0.6% by wt. | 0.7% by wt. | 0.8% by wt. |
| Polyglycerol alkoxylate ester A | 6133 | — | 47840 | — | 85333 | — |
| Polyglycerol alkoxylate ester B | — | 13387 | 20967 | — | — | — |
| Polyglycerol alkoxylate ester C | — | 13867 | 20480 | — | — | — |
| Polyglycerol alkoxylate ester D | — | 5824 | 13067 | 16053 | — | — |
| Polyglycerol alkoxylate ester E | — | — | 9088 | 14133 | — | — |
| Polyglycerol alkoxylate ester F | — | — | 8309 | 13813 | — | — |
| Polyglycerol alkoxylate ester G | — | — | 6905 | 10144 | — | — |
| Polyglycerol alkoxylate ester H | — | — | 13707 | 19998 | — | — |
| Polyglycerol alkoxylate ester I (non-inventive) | — | — | — | — | — | 300 |
| PEG-200 Hydrogenated Glyceryl Palmate; PEG-7 Glyceryl Cocoate (REWODERM ® LI S 80) (non-inventive) | — | — | 75 | — | — | 149 |
| PEG-200 Hydrogenated Glyceryl Palmate; PEG-7 Glyceryl Cocoate (ANTIL ® 200) (non-inventive) | 746 | 1792 | 3676 | 5451 | 8064 | 24213 |
| PEG-120 Methyl Glucose Dioleate (ANTIL ® 120 Plus) (non-inventive) | 3504 | 4128 | 6816 | 9707 | 22720 | 17293 |
| PEG-150 Polyglyceryl-2 Tristearate (and) Laureth-3 (and) Dipropylene Glycol (Genapol ® LT) (non-inventive) | — | — | 2613 | — | 7851 | — |

It becomes clear from the results shown in Table 1 that, when the same amounts of substance are used, higher-viscosity surfactant systems are obtained with the polyglycerol alkoxylate esters according to the invention than with non-inventive polyglyceryl ethoxylate esters, meaning that the required amount of thickener to attain a particular target viscosity is considerably smaller in the case of the polyglycerol alkoxylate esters according to the invention than in the case of the non-inventive ethoxylate esters.

Example 3.2: Improved Thickening Performance of the Polyglycerol Alkoxylate Esters According to the Invention Compared to Non-Inventive Ethoxylate Esters in Aqueous Surfactant Solutions with Low Surfactant Concentration As well as the thickening properties of the polyglycerol alkoxylate esters according to the invention in aqueous surfactant solutions with market standard surfactant concentration that were shown in Example 3.1, the thickening performance was also examined in aqueous surfactant solutions having low surfactant concentration. The viscosities measured for the polyglycerol alkoxylate esters according to the invention after stirring into the aqueous surfactant system are compared in Tables 2 and 3 with the viscosities which were attained by means of non-inventive ethoxylate esters:

TABLE 2

Measured viscosities in mPa s (Brookfield viscometer, 25° C.) of an aqueous surfactant solution containing 9% by weight of a mixture of Sodium Laureth Sulfate and Cocamidopropylbetaine (weight ratio 7:2) and 0.7% sodium chloride and thickener in the amount specified; adjusted to pH 5.5

| Thickener used | Thickener concentration | | |
|---|---|---|---|
| | 1.5% by wt. | 2.0% by wt. | 2.5% by wt. |
| Polyglycerol alkoxylate ester E | 1419 | | 20220 |
| Polyglycerol alkoxylate ester F | 3168 | | 27080 |
| Polyglycerol alkoxylate ester G | 2976 | | 23947 |
| Polyglycerol alkoxylate ester H | | 19397 | 51040 |
| PEG-200 Hydrogenated Glyceryl Palmate; PEG-7 Glyceryl Cocoate (ANTIL ® 200) (non-inventive) | 416 | 1792 | 11220 |
| PEG-120 Methyl Glucose Dioleate (ANTIL ® 120 Plus) (non-inventive) | 832 | 2648 | 11680 |

TABLE 3

Measured viscosities in mPa s (Brookfield viscometer, 25° C.) of an aqueous surfactant solution containing 7% by weight of a mixture of Sodium Laureth Sulfate and Cocamidopropylbetaine (weight ratio 5:2) and 1.5% sodium chloride and thickener in the amount specified; adjusted to pH 5.5

| Thickener used | Thickener concentration | | | | |
|---|---|---|---|---|---|
| | 0.2% by wt. | 0.3% by wt. | 0.5% by wt. | 1.0% by wt. | 1.5% by wt. |
| Polyglycerol alkoxylate ester A | 9643 | 24720 | | | |
| Polyglycerol alkoxylate ester B | | | 46533 | 96173 | 100000 |
| PEG-200 Hydrogenated Glyceryl Palmate; PEG-7 Glyceryl Cocoate (REWODERM ® LI S 80) (non-inventive) | 32 | 42 | | | |
| PEG-200 Hydrogenated Glyceryl Palmate; PEG-7 Glyceryl Cocoate (ANTIL ® 200) (non-inventive) | 778 | 1963 | 7232 | 20160 | 36320 |
| PEG-120 Methyl Glucose Dioleate (ANTIL ® 120 Plus) (non-inventive) | 917 | 2453 | 7733 | 14933 | 18427 |
| PEG-150 Polyglyceryl-2 Tristearate (and) Laureth-3 (and) Dipropylene Glycol (Genapol ® LT) (non-inventive) | | 1344 | 5227 | | |

As shown in Tables 2 and 3, even in those surfactant systems which can be thickened only by means of comparatively high amounts of conventional thickeners because of their low content of wash-active substances, high viscosities can be established by means of comparatively small amounts of the thickeners according to the invention.

Example 3.3: Improved Foam Properties and Improved Skincare Capacity of the Polyglycerol Alkoxylate Esters According to the Invention Compared with Non-Inventive Ethoxylate Esters in Aqueous Surfactant Mixtures For evaluating the foam properties and skincare performance of the polyglycerol alkoxylate ester A of the invention in aqueous surfactant formulations, a sensory handwash test was conducted in comparison with the non-inventive, prior-art ethoxylate ester PEG-200 Hydrogenated Glyceryl Palmate; PEG-7 Glyceryl Cocoate (ANTIL® 200).

A group made up of 10 trained testers washed their hands in a defined way and evaluated foam properties and skin sensation on a rating scale from 1 (very poor) to 5 (very good).

The products were each tested in a standardised surfactant formulation consisting of the standard surfactant system 9% active Sodium Laureth Sulfate and 3% active Cocamidopropyl Betaine (see table 4).

TABLE 4

| Test formulations for the handwash test pH 5.5 | Formulation examples | |
|---|---|---|
| | I | II |
| Texapon ® NSO-IS, BASF Cognis, 28% form (INCI: Sodium Laureth Sulfate) | 32.0% | 32.0% |
| TEGO ® Betain F 50, Evonik Industries AG, 38% form (INCI: Cocamidopropyl Betaine) | 8.0% | 8.0% |
| NaCl | 0.7% | 0.7% |
| Citric acid | q.s. | q.s. |
| Water, demineralised | ad 100 | ad 100 |
| Polyglcyerol alkoxylated ester A; PEG-7 Glcyeryl Cocoate (inventive) | 0.5% | — |
| PEG-200 Hydrogenated Glyceryl Palmate; PEG-7 Glyceryl Cocoate (ANTIL ® 200) (not inventive) | — | 0.8% |

Differences in use concentration are tolerated in order to set an identical viscosity for the formulations; the sensory test results are collated in table 5.

TABLE 5

| Results of the handwash test | | |
|---|---|---|
| | Formulation I | Formulation II |
| Foamability | 3.05 | 2.85 |
| Foam creaminess | 2.90 | 2.75 |
| Wash removal | 3.40 | 3.40 |
| Skin smoothness | 2.10 | 1.95 |
| Skin softness | 2.45 | 2.20 |
| Skin smoothness after 3 min | 3.80 | 3.65 |
| Skin softness after 3 min | 3.80 | 3.65 |

From the test results in table 5 it is evident that the formulation according to the invention, using the polyglycerol alkoxylate ester A according to the invention, leads surprisingly to an improvement in the foamability and the creaminess of the foam, and increases the skin smoothness and softness.

Example 3.4: Improved Mildness of Surfactant Mixtures Comprising Polyglycerol Alkoxylate Esters According to the Invention The mildness of the compositions according to the invention was determined in vitro by means of the Red Blood Cell Test (RBC-Test), which allows the irritant potential of surfactants and surfactant mixtures to be estimated. The test uses a suspension of erythrocytes obtained from pig's blood. Two values are measured: the $H_{50}$, which indicates the amount of surfactant needed to destroy 50% of the erythrocytes, and the DI, which indicates the degree of destruction in % (denaturing) of the haemoglobin by the surfactant or surfactant mixture under investigation, in relation to the destruction caused by a 1% strength Na dodecyl sulfate solution. The ratio formed from the $H_{50}$ (L) and the DI (D), the L/D, is employed in order to estimate the irritant potential of the measured surfactants or surfactant mixtures. The greater the L/D, the milder the classification of the surfactant or surfactant mixture.

In order to evaluate the effect of the polyglycerol alkoxylate ester A according to the invention on the mildness of a surfactant mixture, the L/D was determined for a surfactant mixture containing 7% by weight of a mixture of Sodium Laureth Sulfate and Cocamidopropyl betaine (weight ratio 5:2) and also 1.5% of sodium chloride, in each case once with and once without the polyglycerol alkoxylate ester A according to the invention. The results were as follows (see table 6).

TABLE 6

Results of the Red Blood Cell Test

| | Surfactant mixture | L/D |
|---|---|---|
| III | 5% Sodium Laureth Sulfate, 2% Cocamidopropyl betaine; 1.5% NaCl | 0.5 |
| IV | 5% Sodium Laureth Sulfate, 2% Cocamidopropyl betaine; 1.5 NaCl; 0.1% Polyglycerol Alkoxylate Ester A | 0.6 |

The results of the Red Blood Cell Test from table 6 show that the polyglycerol ethoxylate esters of the invention are beneficial for the mildness of a surfactant mixture while having good foaming and sensory properties.

The following formulation examples show illustrative representatives of a large number of possible compositions according to the invention:

TABLE 7

Further formulation examples

| | 1a | 1b | 2a | 2b | 3a | 3b | 4a | 4b | 5a | 5b | 6a | 6b | 7a | 7b |
|---|---|---|---|---|---|---|---|---|---|---|---|---|---|---|
| Water | to 100% | | | | | | | | | | | | | |
| Polyglycerol alkoxylate ester A | 0.5% | | 0.7% | | 1.0% | | 0.7% | | 2.0% | | 1.0% | | 0.5% | |
| Polyglycerol alkoxylate ester F | | 1.0% | | 1.5% | | 1.7% | | 1.8% | | 3.0% | | 1.8% | | 1.2 |
| Sodium Laureth Sulfate | 9.0% | 9.0% | 7.0% | 7.0% | 6.0% | 6.0% | 5.0% | 5.0% | 5.0% | 5.0% | 8.0% | 8.0% | 9.0% | 9.0% |
| Sodium Lauryl Sulfate | | | | | | | | | | | | | | |
| Cocamidopropyl Betaine | 3.0% | 3.0% | 2.0% | 2.0% | 1.0% | 1.0% | 2.0% | 2.0% | | | | | | |
| Sodium Cocoamphoacetate | | | | | | | | | 2.5% | 2.5% | 2.0% | 2.0% | 3.0% | 3.0% |
| Sodium Laureth Sulfosuccinate | | | | | | | | | 2.5% | 2.5% | | | | |
| Lauryl Glucoside | | | | | | | | | | | | | | |
| Coco-Glucoside | | | | | | | 1.0% | 1.0% | | | 1.0% | 1.0% | | |
| Sodium Cocoyl Glutamate | | | | | | | | | | | | | | |
| Sodium Chloride | 0.3% | 0.3% | 0.7% | 0.7% | 1.0% | 1.0% | 1.5% | 1.5% | 1.5% | 1.5% | 1.5% | 1.5% | 1.0% | 1.0% |
| Cocamide DEA | | | 0.3% | 0.3% | | | | | 0.3% | 0.3% | 0.5% | 0.5% | 0.5% | 0.5% |
| Isostearamide MIPA; Glyceryl Laurate | 0.3% | 0.3% | | | | | 0.5% | 0.5% | | | | | | |
| Xanthan Gum | | | | | 0.1% | 0.1% | | | | | | | 0.5% | 0.5% |
| Glyceryl Glucoside | | | 0.3% | 0.3% | | | | | 0.2% | 0.2% | 0.3% | 0.3% | | |
| Sucrose Cocoate | 0.5% | 0.5% | | | | | | | | | | | 1.0% | 1.0% |
| Glycerin | 1.0% | 1.0% | | | | | | | | | 1.0% | 1.0% | 0.5% | 0.5% |
| PEG-7 Glyceryl Cocoate | | | | | 0.3% | 0.3% | 0.3% | 0.3% | 0.5% | 0.5% | | | | |
| PEG-6 Caprylic/Capric Glycerides | | | 0.2% | 0.2% | | | | | | | | | | |
| Trideceth-9 | | | | | | | | | | | 0.2% | 0.2% | | |
| Polysorbate 20 | 0.3% | 0.3% | | | | | | | | | | | 0.5% | 0.5% |
| PEG-40 Hydrogenated Castor Oil | | | 0.5% | 0.5% | | | | | 0.7% | 0.7% | | | 0.3% | 0.3% |
| Polyglyceryl-4 Caprate | | | | | 0.6% | 0.6% | | | | | | | | |
| Polyquaternium-10 | 0.2% | 0.2% | | | 0.1% | 0.1% | | | | | 0.2% | 0.2% | | |
| Hydroxypropyl Guar Hydroxypropyltrimonium Chloride | | | 0.2% | 0.2% | | | | | 0.3% | 0.3% | | | 0.3% | 0.3% |
| Silicone Quaternium-22 | | | | | 0.2% | 0.2% | | | | | | | 0.3% | 0.3% |
| Dimethicone | | | 0.1% | 0.1% | | | | | | | 0.1% | 0.1% | | |
| Amodimethicone | | | | | 0.1% | 0.1% | | | | | 0.1% | 0.1% | | |
| Persea Gratissima Oil | | | | | 0.1% | 0.1% | | | | | | | | |
| Hydrogenated Castor Oil | | | | | | | 0.1% | 0.1% | | | 0.2% | 0.2% | | |
| Glycol Distearate | | | | | | | | | | | 0.5% | 0.5% | | |
| Zinc Pyrithione | | | | | | | | | | | 0.1% | 0.1% | | |
| Benzophenone-4 | | | 0.1% | 0.1% | | | | | | | 0.1% | 0.1% | | |
| Tetrasodium EDTA | | | | | 0.1% | 0.1% | | | | | 0.1% | 0.1% | | |
| Caffeine | 0.1% | 0.1% | | | | | | | | | 0.1% | 0.1% | 0.1% | 0.1% |
| Hydrolyzed Keratin | | | 0.1% | 0.1% | | | | | | | | | 0.1% | 0.1% |
| Panthenol | 0.1% | 0.1% | | | | | 0.1% | 0.1% | 0.1% | 0.1% | 0.1% | 0.1% | 0.1% | 0.1% |
| Citric Acid | to pH 5.5 | | | | | | | | | | | | | |
| Perfumes, Dyes, Preservatives | q.s. | | | | | | | | | | | | | |

TABLE 7-continued

Further formulation examples

| | 8a | 8b | 9a | 9b | 10a | 10b | 11a | 11b | 12a | 12b | 13a | 13b |
|---|---|---|---|---|---|---|---|---|---|---|---|---|
| Water | to 100% | | | | | | | | | | | |
| Polyglycerol alkoxylate ester A | 0.7% | | 1.2% | | 3.5% | | 4.0% | | 3.5% | | 3.0% | |
| Polyglycerol alkoxylate ester F | | 1.5% | | 2.2% | | 5.0% | | 5.0% | | | | |
| Sodium Laureth Sulfate | | | | | | | | | | | | |
| Sodium Lauryl Sulfate | 6.0% | 6.0% | 5.0% | 5.0% | | | | | 3.5% | 3.5% | 6.0% | 6.0% |
| Cocamidopropyl Betaine | 3.0% | 3.0% | 5.0% | 5.0% | 6.0% | 6.0% | | | 2.0% | 2.0% | | |
| Sodium Cocoamphoacetate | 3.0% | 3.0% | | | | | 3.0% | 3.0% | | | | |
| Sodium Laureth Sulfosuccinate | | | 2.0% | 2.0% | | | | | | | | |
| Lauryl Glucoside | | | | | 5.0% | 5.0% | 3.0% | 3.0% | | | 3.5% | 3.5% |
| Coco-Glucoside | | | | | 1.0% | 1.0% | 5.5% | 5.5% | 2.0% | 2.0% | 2.5% | 2.5% |
| Sodium Cocoyl Glutamate | | | | | 1.0% | 1.0% | 1.5% | 1.5% | 0.5% | 0.5% | | |
| Sodium Chloride | 1.5% | 1.5% | 1.0% | 1.0% | | | | | | | 1.0% | 1.0% |
| Cocamide DEA | 1.0% | 1.0% | | | 1.0% | 1.0% | | | | | | |
| Isostearamide MIPA; Glyceryl Laurate | | | | | | | 0.2% | 0.2% | 1.0% | 1.0% | 0.5% | 0.5% |
| Xanthan Gum | | | | | 0.7% | 0.7% | 2.0% | 2.0% | — | — | — | — |
| Glyceryl Glucoside | 0.5% | 0.5% | 0.3% | 0.3% | | | 0.2% | 0.2% | | | | |
| Sucrose Cocoate | | | 0.3% | 0.3% | 0.2% | 0.2% | — | — | 1.0% | 1.0% | 1.0% | 1.0% |
| Glycerin | 1.0% | 1.0% | 0.3% | 0.3% | 0.4% | 0.4% | 1.5% | 1.5% | 0.5% | 0.5% | 1.0% | 1.0% |
| PEG-7 Glyceryl Cocoate | | | | | | | | | | | 0.5% | 0.5% |
| PEG-6 Caprylic/Capric Glycerides | | | 0.3% | 0.3% | | | | | 0.2% | 0.2% | 0.2% | 0.2% |
| Trideceth-9 | | | 0.2% | 0.2% | | | | | | | | |
| Polysorbate 20 | | | | | | | | | 0.3% | 0.3% | 0.2% | 0.2% |
| PEG-40 Hydrogenated Castor Oil | | | 0.5% | 0.5% | | | | | 1.0% | 1.0% | — | — |
| Polyglyceryl-4 Caprate | 2.0% | 2.0% | | | 0.5% | 0.5% | | | | | 0.5% | 0.5% |
| Polyquaternium-10 | 0.1% | 0.1% | | | | | | | 0.2% | 0.2% | | |
| Hydroxypropyl Guar Hydroxypropyltrimonium Chloride | 0.2% | 0.2% | 0.2% | 0.2% | 0.2% | 0.2% | 0.2% | 0.2% | | | | |
| Silicone Quaternium-22 | | | 0.3% | 0.3% | | | | | | | | |
| Dimethicone | | | | | | | | | 0.1% | 0.1% | | |
| Amodimethicone | 0.1% | 0.1% | 0.1% | 0.1% | | | | | 0.5% | 0.5% | | |
| Persea Gratissima Oil | 0.1% | 0.1% | | | 0.1% | 0.1% | 0.2% | 0.2% | 0.1% | 0.1% | 0.2% | 0.2% |
| Hydrogenated Castor Oil | | | | | | | 0.3% | 0.3% | 0.5% | 0.5% | 0.5% | 0.5% |
| Glycol Distearate | | | 0.5% | 0.5% | | | | | | | | |
| Zinc Pyrithione | | | — | — | — | — | — | — | 0.1% | 0.1% | | |
| Benzophenone-4 | 0.1% | 0.1% | 0.1% | 0.1% | — | — | 0.1% | 0.1% | 0.1% | 0.1% | | |
| Tetrasodium EDTA | | | 0.1% | 0.1% | — | — | — | — | 0.1% | 0.1% | | |
| Caffeine | | | — | — | — | — | — | — | 0.1% | 0.1% | | |
| Hydrolyzed Keratin | | | | | 0.1% | 0.1% | 0.2% | 0.2% | 0.1% | 0.1% | | |
| Panthenol | 0.1% | 0.1% | 0.1% | 0.1% | 0.1% | 0.1% | | | 0.1% | 0.1% | 0.1% | 0.1% |
| Citric Acid | to pH 5.5 | | | | | | | | | | | |
| Perfumes, Dyes, Preservatives | q.s. | | | | | | | | | | | |

TABLE 8

Further formulation examples

| | 14a | 14b | 15a | 15b | 16a | 16b | 17a | 17b | 18a | 18b | 19a | 19b | 20a | 20b |
|---|---|---|---|---|---|---|---|---|---|---|---|---|---|---|
| Water | to 100% | | | | | | | | | | | | | |
| Polyglycerol alkoxylate ester A | 0.3% | | 0.5 | | 0.6 | | 1.5% | | 0.5% | | 0.4 | | 1.3% | |
| Polyglycerol alkoxylate ester F | | 0.7 | | 1.5% | | 1.7% | | 2.5% | | 1.4% | | 1.0% | | 2.5% |
| Sodium Laureth Sulfate | 9% | 9% | 8.0% | 8.0% | 6.0% | 6.0% | | | 6% | 6% | 4.5% | 4.5% | | |
| Coco-Betaine | 3% | 3% | 3.0% | 3.0% | | | 5.5% | 5.5% | | | | | | |
| Cocamidopropyl Betaine | | | | | 2.0% | 2.0% | | | 1.5% | 1.5% | | | 5.0% | 5.0% |
| Sodium Cocoamphoacetate | | | | | 2.0% | 2.0% | 3.0% | 3.0% | | | 4.5% | 4.5% | | |
| Disodium Lauryl Sulfosuccinate | | | | | 1.0% | 1.0% | | | 1.5% | 1.5% | | | | |
| Decyl Glucoside | | | 1.0% | 1.0% | | | 2.0% | 2.0% | 1.0% | 1.0% | | | 3.0% | 3.0% |
| Sodium Cocoyl Glutamate | | | | | | | 2.5% | 2.5% | | | | | | |
| Sodium Cocoyl Glycinate | | | | | | | | | | | | | 2.0% | 2.0% |
| Sodium Lauroyl Isethionate | | | | | | | | | | | | | | |
| Sodium Chloride | 0.7% | 0.7% | 0.7% | 0.7% | 1.0% | 1.0% | | | 1.0% | 1.0% | 1.7% | 1.7% | 1.5% | 1.5% |
| Cocamide MEA | | | 0.5% | 0.5% | | | 1.0% | 1.0% | | | | | | |
| Xanthan Gum | | | | | | | | | | | | | | |
| Hydroxyethyl Ethylcellulose | | | | | | | 0.3% | 0.3% | | | | | | |
| Acrylates/C10-30 Alkyl Acrylate Crosspolymer | 0.5% | 0.5% | | | | | | | | | | | 0.5% | 0.5% |
| Stearic Acid | | | | | 0.3% | 0.3% | | | | | | | | |
| Sucrose Cocoate | 0.5% | 0.5% | 0.4% | 0.4% | | | 1.0% | 1.0% | | | 0.3% | 0.3% | | |
| Glycerin | 1.5% | 1.5% | 0.3% | 0.3% | | | 0.5% | 0.5% | 1.0% | 1.0% | | | 0.3% | 0.3% |
| PEG-40 Hydrogenated Castor Oil | | | 1.0% | 1.0% | | | | | | | | | | |

TABLE 8-continued

| Further formulation examples | | | | | | | | | | | | | |
|---|---|---|---|---|---|---|---|---|---|---|---|---|---|
| Polyglyceryl-4 Caprate | 0.5% | 0.5% | | | | | 0.5% | 0.5% | | | | | |
| Polyquaternium-11 | | | 0.2% | 0.2% | | | | | | | | 0.1% | 0.1% |
| Guar Hydroxypropyltrimonium Chloride | | | | | 0.3% | 0.3% | 0.2% | 0.2% | | | | 0.2% | 0.2% |
| Dimethicone | | | 0.3% | 0.3% | | | | | | | | | |
| Aminopropyl Dimethicone | | | | | 0.5% | 0.5% | | | | | | | |
| PEG-3 Distearate | | | 0.5% | 0.5% | | | | | | | | | |
| Benzophenone-4 | | | 0.1% | 0.1% | 0.2% | 0.2% | | | | | | | |
| Menthol | 0.1% | 0.1% | | | 0.1% | 0.1% | | | 0.1% | 0.1% | | | |
| Caffeine | | | | | 0.1% | 0.1% | | | | | | 0.1% | 0.1% |
| Benzyl Alcohol | 0.1% | 0.1% | | | | | | | | | | | |
| Coumarin | 0.1% | 0.1% | | | 0.1% | 0.1% | 0.1% | 0.1% | | | | | |
| Hydrolyzed Wheat Protein | | | | | 0.1% | 0.1% | | | 0.1% | 0.1% | | 0.1% | 0.1% |
| Panthenol | 0.1% | 0.1% | 0.1% | 0.1% | | | 0.1% | 0.1% | 0.1% | 0.1% | 0.1% 0.1% | 0.1% | 0.1% |
| Sodium Hydroxide, 25% | | | | | 0.6% | 0.6% | | | | | | 0.8% | 0.8% |
| Citric Acid | to pH 6.0 | | | | | | | | | | | | |
| Perfumes, Dyes, Preservatives | q.s | | | | | | | | | | | | |

| | 21a | 21b | 22a | 22b | 23a | 23b | 24a | 24b | 25a | 25b | 26a | 26b |
|---|---|---|---|---|---|---|---|---|---|---|---|---|
| Water | | | | | | | | | | | | |
| Polyglycerol alkoxylate ester A | 3.5% | | 2.7% | | 1.0% | | 1.2% | | 2.5% | | | |
| Polyglycerol alkoxylate ester F | | 5.0% | | 4.5% | | 2.2% | 2.5% | 2.5% | | 3.5% | | |
| Sodium Laureth Sulfate | | | | | 4.0% | 4.0% | | | | | | |
| Coco-Betaine | | | | | 2.0% | 2.0% | | | | | | |
| Cocamidopropyl Betaine | | | 3.5% | 3.5% | | | 5.0% | 5.0% | 7.0% | 7.0% | 6.0% | 6.0% |
| Sodium Cocoamphoacetate | 5.0% | 5.0% | | | 2.0% | 2.0% | | | | | 2.0% | 2.0% |
| Disodium Lauryl Sulfosuccinate | | | | | 1.0% | 1.0% | | | | | 2.0% | 2.0% |
| Decyl Glycoside | 4.0% | 4.0% | 5.0% | 5.0% | | | 2.0% | 2.0% | | | | |
| Sodium Cocoyl Glutamate | 2.0% | 2.0% | 2.5% | 2.5% | 1.5% | 1.5% | 1.0% | 1.0% | | | | |
| Sodium Cocoyl Glycinate | | | | | | | | | 3.0% | 3.0% | | |
| Sodium Lauroyl Isethionate | 1.0% | 1.0% | | | 1.0% | 1.0% | 0.5% | 0.5% | 2.0% | 2.0% | | |
| Sodium Chloride | | | | | 1.0% | 1.0% | 1.0% | 1.0% | 1.0% | 1.0% | 1.0% | 1.0% |
| Cocamide MEA | 0.2% | 0.2% | 0.5% | 0.5% | | | 0.3% | 0.3% | | | | |
| Xanthan Gum | | | 0.1% | 0.1% | 0.2% | 0.2% | 0.3% | 0.3% | 0.2% | 0.2% | | |
| Hydroxyethyl Ethylcellulose | 0.1% | 0.1% | | | | | | | 0.5% | 0.5% | | |
| Acrylates/C10-30 Alkyl Acrylate Crosspolymer | 0.4% | 0.4% | | | | | | | | | | |
| Stearic Acid | | | | | 0.1% | 0.1% | 0.5% | 0.5% | 0.5% | 0.5% | | |
| Sucrose Cocoate | | | 0.2% | 0.2% | 0.3% | 0.3% | 0.3% | 0.3% | | | 0.2% | 0.2% |
| Glycerin | 0.5% | 0.5% | 1.0% | 1.0% | | | 1.0% | 1.0% | 2.0% | 2.0% | 1.5% | 1.5% |
| PEG-40 Hydrogenated Castor Oil | | | | | 0.3% | 0.3% | | | | | | |
| Polyglyceryl-4 Caprate | 2.6% | 2.6% | | | | | | | | | | |
| Polyquaternium-11 | | | | | 0.2% | 0.2% | 0.3% | 0.3% | | | 0.1% | 0.1% |
| Guar Hydroxypropyltrimonium Chloride | 0.3% | 0.3% | 0.2% | 0.2% | 0.1% | 0.1% | | | | | | |
| Dimethicone | | | | | 0.2% | 0.2% | | | | | | |
| Aminopropyl Dimethicone | | | | | | | | | | | | |
| PEG-3 Distearate | | | | | 0.5% | 0.5% | | | 0.5% | 0.5% | | |
| Benzophenone-4 | | | | | 0.2% | 0.2% | 0.1% | 0.1% | | | | |
| Menthol | 0.1% | 0.1% | | | 0.1% | 0.1% | 0.1% | 0.1% | | | | |
| Caffeine | | | | | 0.1% | 0.1% | 0.1% | 0.1% | | | 0.1% | 0.1% |
| Benzyl Alcohol | 0.1% | 0.1% | | | 0.1% | 0.1% | | | 0.1% | 0.1% | | |
| Coumarin | | | 0.1% | 0.1% | | | 0.1% | 0.1% | | | | |
| Hydrolyzed Wheat Protein | | | 0.2% | 0.2% | 0.1% | 0.1% | | | | | | |
| Panthenol | 0.1% | 0.1% | 0.1% | 0.1% | | | 0.1% | 0.1% | 0.1% | 0.1% | | |
| Sodium Hydroxide, 25% | 0.5% | 0.5% | | | | | | | | | | |
| Citric Acid | to pH 6.0 | | | | | | | | | | | |
| Perfumes, Dyes, Preservatives | q.s. | | | | | | | | | | | |

The invention claimed is:

1. A polyglycerol alkoxylate ester of the general formula (I)

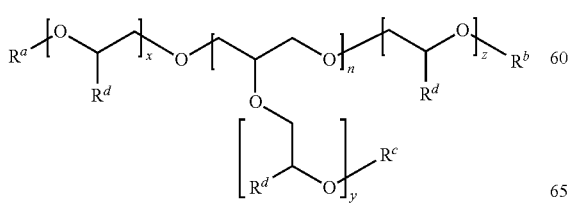

wherein
$R^a$, $R^b$, $R^c$=identical or different and independently selected from H and acyl radical of fatty acid with from 16 to 22 carbon atoms, wherein an average of 3 to 6 of the $R^a$, $R^b$, $R^c$ radicals per molecule are not H,
$R^d$=H,
n=1.5 to 16,
x, y, z=identical or different and independently 30 to 200, wherein the sum total of $x+n \cdot y+z$ averages 251 to 750.

2. The polyglycerol alkoxylate ester according to claim 1, wherein
$R^a$, $R^b$, $R^c$=H or acyl radical of a fatty acid having 16 to 22 carbon atoms, wherein an average of 3.5 to 6 of the $R^a$, $R^b$, $R^c$ radicals per molecule are not H, n=3 to 11, x, y, z=identical or different and independently 40 to 80, wherein the sum total of x+n·y+z for each molecule averages 300 to 750.

3. The polyglycerol alkoxylate ester of claim 1 obtained by a process for preparing polyglycerol alkoxylate ester, comprising the process steps of
   A) providing a polyglycerol having a polymerization level n of 1.5 to 16,
   B) alkoxylating the polyglycerol with 251 to 750 mol of alkylene oxide selected from the group consisting of ethylene oxide, propylene oxide, butylene oxide, and dodecene oxide per mole of polyglycerol used in the overall process is used in process step B), and
   C) esterifying with 3 to 6 mol of at least one selected from organic acids per mole of polyglycerol used in the overall process.

4. A formulation comprising at least one polyglycerol alkoxylate ester according to claim 3.

5. An aqueous formulation comprising at least one polyglycerol alkoxylate ester according to claim 1.

6. The aqueous formulation according to claim 5 comprising at least one surfactant.

7. The aqueous formulation according to claim 6, comprising one or more surfactants in a total amount of 0.1% by weight to 20% by weight, where the percentages by weight relate to the overall composition.

8. The aqueous formulation according to claim 6, comprising one or more surfactants in a total amount of 1.0% by weight to 15% by weight, where the percentages by weight relate to the overall composition.

9. The aqueous formulation according to claim 5, comprising at least one optionally alkoxylated alcohol and/or at least one optionally alkoxylated carboxylic ester.

10. The aqueous formulation according to claim 9, wherein the polyglycerol alkoxylate ester is present in an amount of 30% to 70% by weight, based on the overall formulation.

11. A thickener comprising the polyglycerol alkoxylate ester according to claim 1.

12. A skincare product comprising the polyglycerol alkoxylate ester according to claim 1.

13. A foam stabilizer comprising the polyglycerol alkoxylate ester according to claim 1.

14. A cosmetic formulation for reducing irritation comprising the polyglycerol alkoxylate ester according to claim 1.

15. The polyglycerol alkoxylate ester according to claim 1, wherein
    $R^a$, $R^b$, $R^c$=H or acyl radical of a fatty acid having 16 to 22 carbon atoms,
    with the proviso that an average of 3.5 to 5.5 of the $R^a$, $R^b$, $R^c$ radicals per molecule are not H,
    n=4 to 9,
    x, y, z=identical or different and independently 30 to 100, with the proviso that the sum total of x+n·y+z averages 300 to 600.

16. A process for preparing polyglycerol alkoxylate ester, comprising the process steps of
    A) providing a polyglycerol having a polymerization level n of 1.5 to 16,
    B) alkoxylating the polyglycerol with 251 to 750 mol of alkylene oxide selected from the group consisting of ethylene oxide, propylene oxide, butylene oxide, and dodecene oxide per mole of polyglycerol used in the overall process is used in process step B), and
    C) esterifying with 3 to 6 mol of at least one selected from organic acids per mole of polyglycerol used in the overall process.

17. The process according to claim 16, wherein the process steps are conducted in the sequence "A), C), B)".

18. The process according to claim 16, wherein
    a polyglycerol having a polymerization level of 3 to 11 is used in process step A), 300 to 750 mol of ethylene oxide per mole of polyglycerol used in the overall process is used in process step B) and
    3.5 to 6 mol of at least one selected from fatty acids having 16 to 22 carbon atoms per mole of polyglycerol used in the overall process is used in process step C).

19. The process according to claim 16, wherein
    a polyglycerol having a polymerization level of 4 to 9 is used in process step A),
    300 to 600 mol of ethylene oxide per mole of polyglycerol used in the overall process is used in process step B) and
    3.5 to 5.5 mol of at least one selected from fatty acids having 16 to 22 carbon atoms per mole of polyglycerol used in the overall process is used in process step C).

20. The polyglycerol alkoxylate ester of claim 19 wherein the process steps are conducted in the sequence "A), C), B)".

* * * * *